US005814312A

United States Patent [19]
Reich et al.

[11] Patent Number: 5,814,312
[45] Date of Patent: Sep. 29, 1998

[54] COMPOSITION AND PROCESS FOR DEDUCING ODORS FROM ANIMAL DISCHARGES

[75] Inventors: Ronald C. Reich, Snellville, Ga.; Willow Zoè, Tacoma, Wash.

[73] Assignee: Weaser, Inc., Highland Beach, Fla.

[21] Appl. No.: 694,196

[22] Filed: Aug. 8, 1996

Related U.S. Application Data

[63] Continuation of Ser. No. 385,719, Feb. 8, 1995.
[51] Int. Cl.⁶ ........................................ A61L 11/00
[52] U.S. Cl. ............................ 424/76.6; 424/400
[58] Field of Search ..................... 424/76.6, 400

[56] References Cited

U.S. PATENT DOCUMENTS

| | | | |
|---|---|---|---|
| 490,797 | 1/1893 | Woolf | 424/661 |
| 2,794,762 | 6/1957 | Westcott | 424/76.1 |
| 3,123,521 | 3/1964 | Wentworth et al. | 167/17 |
| 3,124,459 | 3/1964 | Erwin | 424/76.1 |
| 3,124,460 | 3/1964 | Erwin | 424/76.1 |
| 3,147,124 | 9/1964 | Wentworth et al. | 99/116 |
| 3,591,515 | 7/1971 | Lovely | 252/187 |
| 3,857,946 | 12/1974 | Shibata | 424/266 |
| 4,086,333 | 4/1978 | Bredwell | 424/615 |
| 4,296,102 | 10/1981 | Laso | 424/130 |
| 4,296,103 | 10/1981 | Laso | 424/130 |
| 4,362,753 | 12/1982 | Barta | 426/332 |
| 4,737,307 | 4/1988 | Brown | 510/131 |
| 4,808,389 | 2/1989 | Ratcliffe | 424/53 |
| 4,818,519 | 4/1989 | Ratcliff | 424/53 |
| 4,851,213 | 7/1989 | Ratcliff | 424/53 |
| 4,996,055 | 2/1991 | Kurasawa | 424/442 |
| 5,015,467 | 5/1991 | Smitherman | 424/440 |
| 5,076,960 | 12/1991 | Hutchings et al. | 252/186.33 |
| 5,294,458 | 3/1994 | Fujimori | 426/635 |
| 5,360,574 | 11/1994 | Iwahashi | 252/187.21 |

FOREIGN PATENT DOCUMENTS

| | | |
|---|---|---|
| 0347320 | 12/1989 | European Pat. Off. . |
| 0423816 | 12/1991 | European Pat. Off. . |
| 90161317 | 10/1988 | Japan . |
| 1305040 | 1/1973 | United Kingdom . |
| 9527472 | 10/1995 | WIPO . |

OTHER PUBLICATIONS

R.C. Steele® Catalog (Pet Products, pp. 2 and 60); (Mid-summer 1996).
Elimina™ (bottle labels) Pet–Tech, Inc. (2 pages) (Date: Unknown).
R.P. Adams, Chemical Treatment of Farm Wastes, 32 ADAS Quarterly Review, 173–184 (1979)(Abstract From CAB International, Walling Ford, Oxon, GB).
K. Pedersen and N. Jahromi, Inactivation of Bacteria with SMAC—A Stable Solution of Chlorine Dioxide in Water, 49 VATTEN 264–270 (Lund 1993)(English translation).
Oxyfresh™ Pet Gel, (tube label) Oxyfresh Worldwide, Inc. (2 pages)(Date: Unknown).
Oxyfresh™ Pet Deoderizer, (bottle label) Oxyfresh Worldwide, Inc. (2 pages)(Date:Unknown).
Oxyfresh® Product Catalog (Pet Products, p. 9); Oxyfresh Worldwide, Inc.; (Feb. 1995).
Freedom of Choice (Franchising Brochure, p. 5), Oxyfresh Worldwide, Inc.; (Nov. 1995).
*Cats Magazine*, Advertisement "Premira For Cats", p. 42, Mar. 1994, p. 37, Apr. 1994.
Du, *Chemical Abstracts*, vol. 120, 1992, #33986.
King, *World Patents Abstract*, for JP 59006059, 1984, #84–45591.
Sumitomo, *World Patents Abstract* for JP 52113396, 1977, #77–78621Y.

*Primary Examiner*—Thurman K. Page
*Assistant Examiner*—Kathryne E. Shelborne
*Attorney, Agent, or Firm*—Baker & Botts, L.L.P.

[57] ABSTRACT

A composition for reducing odors emanating from animal discharges includes de-ionized water filtered by reverse osmosis; chlorine dioxide in a range of about 0.01% to 0.1% by weight; and acetic acid in sufficient quantity to adjust the pH of the composition to a range of about 9.2 to 9.4. A process for manufacturing such a composition includes the steps of providing de-ionized water filtered by reverse osmosis; adding a source of chlorine dioxide to said water in an amount in a range of about 0.01% to 0.1% by weight; and adding acetic acid to the water in sufficient quantity to adjust the pH of the composition to a range of about 9.2 to 9.4. The source of chlorine dioxide and the acetic acid are added to the water, in such a manner that a dissolved oxygen content of the composition is less than about 1 ppm. The composition may be part of a product with an ultra-violet radiation proof container for storing the composition and a spray applicator, which applies a dosage of about 0.05 ounces per spray ($0.14 \times 10^{-5}$ m³ per spray).

47 Claims, No Drawings

1

COMPOSITION AND PROCESS FOR DEDUCING ODORS FROM ANIMAL DISCHARGES

This application is a continuation of application Ser. No. 08/385,719, filed Feb. 8, 1995 entitled COMPOSITION AND PROCESS FOR REDUCING ODORS FROM ANIMAL DISCHARGES (Amended).

BACKGROUND OF THE INVENTION

1. Field of the Invention

This invention relates to compositions for reducing odors emanating from animal discharges, such as feces; urine; glandular secretions, e.g., sexual excitants emitted by female animals in estrus; and the like. Further, it relates to processes for manufacturing such compositions, methods for using such compositions, and packages for storing, transporting, and applying such compositions. In particular, it relates to such compositions that may be added to animal food for ingestion by the animal.

2. Description of the Related Art

Many attempts have been made over the years to reduce or eliminate fecal, urine and sexual excrement odors created by animals, such as household pets. Household pets, e.g., cats, dogs, ferrets, and Vietnamese Pot-Bellied pigs, are very important members of millions of households. Also, millions of cats and dogs are euthenized each year due to the lack of loving homes. Reducing and eliminating pet odors at the source will make pet ownership more desirable. This will reduce euthenizing of many animals.

Animal's digestive processes generate sulphur and nitrogen compounds, which contribute to urine and fecal odors. Attempts have been made to cover or mask such odors by spraying the animal with or inducing the animal to ingest chlorophyll and related compounds. Other proposed solutions have included food additives containing water-soluble copper and iron compounds and a water-soluble phosphate. A portion of the metals present in such additives may be in the form of inedible water soluble ionizable salts including chlorides.

Attempts have also been made to eliminate the odor of sexual excitants from the discharge of female animals in estrus. These attempts have included the topical and suppository application of compounds incorporating stabilized chlorine dioxide. Such compounds included groups formed by the reaction of chlorine dioxide with sodium carbonate peroxide and chlorine dioxide with sodium perborate. Topical application of the compound may be in ointment form to the region of the animal where the excitant is present or by the placement of a suppository containing the compound into the vaginal orifice of the animal. Additionally, the compound can be applied by spraying or swabbing an aqueous solution of it onto the genital region of the animal in heat.

Despite these attempts a safe and effective composition for reducing odor from animal discharges, which may be easily administered and has a suitable shelf-life, has not been discovered.

SUMMARY OF THE INVENTION

Accordingly, a need has arisen for a safe, e.g., non-toxic, and effective composition for reducing odors from animal discharges. An object of the present invention is to provide a composition for reducing odors from animal discharges that may be accurately applied to an animal's daily food ration without upsetting the normal eating habits of the animal. It is a further object that the composition is safe, eg., non-toxic, and does not detract from the nutritional balance of the food ration. Yet another object of the present invention is to provide a composition for reducing odors from animal discharges that is easily and inexpensively manufactured and has a suitable shelf-life. Still another object of the present invention is that it is chlorophyll free.

One embodiment of the invention in its broadest form provides a composition for reducing odors emanating from animal discharges comprises water with low mineral content expressed as a calcium carbonate content less than about 1000 ppm; chlorine dioxide in a range of about 0.01% to 0.5% by weight; and a food grade acidulent in sufficient quantity to adjust the pH of the composition to a to greater than about 7.

Another embodiment of the invention provides a process for manufacturing a composition for reducing odors emanating from animal discharges. The process comprising the steps of providing the low mineral content water with a calcium carbonate content less than about 1000 ppm; adding chlorine dioxide to the water in an amount less than about 0.5% by weight; and adding a food grade acidulent to the water in sufficient quantity to adjust the pH of the composition to greater than about 7. The source of chlorine dioxide and the food grade acidulent may be added to the water, such that a dissolved oxygen content of the composition of less than about 5 ppm is achieved, e.g., by low shear mixing.

In yet another embodiment of the invention, there is provided a product for reducing odors emanating from animal discharges. The product comprises a composition including low mineral content water with a calcium carbonate content less than about 1000 ppm; chlorine dioxide less than about 0.5 % by weight; and a food grade acidulent in sufficient quantity to adjust the pH of the composition to greater than about 7; disposed in a container for storing the composition that comprises a material that substantially blocks the transmission of ultra-violet radiation.

Other objects, features, and advantages will be apparent from the following description of the invention.

DETAILED DESCRIPTION OF PREFERRED EMBODIMENTS

The composition of matter of the present invention is useful for reducing odors emanating from animal discharges, such as feces; urine; glandular secretions, e.g., sexual excitants emitted by female animals in estrus; and the like. The composition includes (1) water having a low mineral content, i.e., a calcium carbonate content less than about 1000 ppm and preferably, less than about 500 ppm; (2) chlorine dioxide is present in an amount less than about 0.5%, and preferably, less than about 0.1% by weight; and (3) a food grade acidulent in sufficient quantity to adjust the pH of the composition to a value greater than about 7 and preferably greater than about 9. Most preferably, (1) the water has a calcium carbonate content less than about 300 ppm, such as de-ionized water filtered by reverse osmosis or distilled water; (2) the chlorine dioxide is present in a range of about 0.01 to 0.1% by weight; and (3) the food grade acidulent in sufficient quantity to adjust the pH of the composition to a range of about 9.2 to 9.4.

The food grade acidulent may be selected from a group consisting of phosphoric acid, citric acid, malic acid, and acetic acid. If acetic acid is chosen as the food grade acidulent, distilled vinegar may be added to the composition. Further, it is preferred that the composition be prepared, such that it has a dissolved oxygen content less than about 5 ppm. Preferably, it has a dissolved oxygen content of less than about 2 ppm, and still more preferably, less than 1 ppm.

The composition may be manufactured by a process comprising the steps of: (1) providing water with a calcium carbonate content less than about 1000 ppm and preferably less than about 500 ppm; (2) adding chlorine dioxide to the water in an amount less than about 0.5% and preferably less than about 0.1% by weight; and (3) adding a food grade acidulent to the water in sufficient quantity to adjust the pH of the composition to a value greater than about 7 and preferably greater than about 9. Most preferably, (1) the water has a calcium carbonate content less than about 300 ppm, such as de-ionized water filtered by reverse osmosis or distilled water; (2) the chlorine dioxide is added in a range of about 0.01 to 0.1% by weight; and (3) the food grade acidulent is added in sufficient quantity to adjust the pH of the composition to a value in a range of about 9.2 to 9.4.

A stabilized chlorine dioxide, such as Anthium Dioxide®, may be added to the water as the source of chlorine dioxide. Anthium Dioxides® is a registered trade mark for a 5% chlorine dioxide solution manufactured by International Dioxide Inc., Clark, N.J. Anthium Dioxide® is an aqueous solution of sodium chlorate which provides chlorine dioxide under formulation conditions. If Anthium Dioxide® is used as the source of chlorine dioxide, it may be present in the solution in a range of 5% to 10% by weight. Alternatively, Oxine® or Puregene®, which are registered trade marks for 2% chlorine dioxide solutions manufactured by International Biocide, Norman, Okla., may be used as the source of chlorine dioxide.

The manner of blending of water and the other ingredients is important to the shelf-life of the composition. Vigorous mixing may incorporate dissolved oxygen into the composition and shorten the shelf-life of the composition. It is preferred that the source of chlorine dioxide and the food grade acidulent are blended into the water, in such a manner that a dissolved oxygen content of the composition is less than about 5 ppm. Preferably, the final solution has a dissolved oxygen content of less than about 2 ppm, and still more preferably, less than about 1 ppm. This may be accomplished, for example, by mixing the components with low shear, e.g., by hand mixing, so that there is no unnecessary agitation of the composition and no excess oxygen is introduced. Alternatively, the composition may be mixed using known mixing devices under conditions which preclude the introduction of excess oxygen, such as under a cover of inert gas, e.g., nitrogen.

A product for reducing odors emanating from animal discharges may include the composition, as described herein, and disposed in a container for storing the composition, which comprises a material, e g., such as metal, opaque plastic, or the like, that substantially blocks the transmission of ultra-violet radiation. Protection against ultra-violet radiation helps prevent the chemical degradation of the composition and is important in applications in which a longer shelf-life is desired. Because the purchased product may be used over a period of weeks or months, extending the shelf-life is important to the commercial success of the product. The product may further include application means for applying measured amounts of the composition to the animal or animal food. Suitable application means is a spray applicator. Preferably, such a spray applicator applies a dosage in a range of about 0.025 to 0.075 ounces per spray, e.g., 0.05 ounces per spray ($0.14 \times 10^{-5}$ m$^3$ per spray).

The method for using the composition of the present invention comprises the steps of applying a dosage of the composition, as described herein, in an amount effective to reduce odors to food rations and feeding the food rations to an animal. Preferably; the dosage is applied using application means, which delivers about 0.05 ounces per application ($0.14 \times 10^{-5}$ m$^3$ per application). A suitable application has been found to be at least about three sprays per day applied to each food ration. This results in a dosage of about one ounce per week ($2.96 \times 10^{-5}$ m$^3$ per week).

The invention may be further understood by a consideration of the following non-limiting example.

EXAMPLE

A composition for reducing odors emanating from animal discharges was prepared by providing 29.75 U.S. fluid ounces ($8.81 \times 10^{-4}$ m$^3$) purified water and adding 2.25 U.S. fluid ounces ($6.66 \times 10^{-5}$ m$^3$) of Anthium Dioxide® and 4 drops of distilled white table vinegar. This composition was effective in reducing odors emanating from cat feces and urine.

Two groups of 40 cats were divided as follows:
Control Group—10 pens with 4 cats per pen
Test Group—10 pens with 4 cats per pen.
Both control and test pens contained wooden litter boxes with sand as the litter media. The cats were fed the same food in equal amounts. Uniform doses of the above composition were applied to each food ration using a spray applicator. The spray applicator delivered a dosage of about 0.05 ounces per spray ($0.14 \times 10^{-5}$ m$^3$ per spray). Three sprays were applied to each food ration and each test cat was fed once per day. This amounts to 21 sprays per cat per week or about one ounce ($2.96 \times 10^{-5}$ m$^3$) of the composition per cat per week. At the conclusion of the test, it was discovered that the test litter box accumulation of urine and feces was virtually odor free to the average human nose whereas the control litter box accumulations had the usual strong odors. Further, over five cat generations tested, no adverse effects were noted in the number of kittens born or the health of the kittens or nursing mothers.

Other embodiments of the invention will be apparent to persons skilled in the art from a consideration of this specification or the practice of the invention disclosed herein. It is intended that the specification and the example be considered as exemplary only, with the true scope and spirit of the invention being indicated by the following claims.

We claim:
1. A composition for reducing odors emanating from animal discharges consisting essentially of:
   (a) water with a calcium carbonate content less than about 1000 ppm;
   (b) chlorine dioxide in an amount effective to reduce odors emanating from animal discharges; and
   (c) an acidulent in an amount sufficient to adjust the pH of the composition to a value greater than above 7.
2. The composition of claim 1, wherein said water has a calcium carbonate content less than about 500 ppm.
3. The composition of claim 1, wherein said water has a calcium carbonate content less than about 300 ppm.
4. The composition of claim 1, wherein said food grade acidulent is present in an amount sufficient to adjust the pH of the composition to a value greater than about 9.
5. The composition of claim 1, wherein said food grade acidulent is present in an amount sufficient to adjust the pH of the composition to a value grater than about 9.2 to 9.4.
6. The composition of claim 1, wherein said water is de-ionized water filtered by reverse osmosis.

7. The composition of claim 1, wherein said water is distilled water.

8. The composition of claim 1, wherein said food grade acidulent is selected from the group consisting of phosphoric acid, citric acid, malic acid and acetic acid.

9. The composition of claim 1, wherein said food grade acidulent is distilled vinegar.

10. The composition of claim 1, wherein said source of chlorine dioxide and said food grade acidulent are added to said water, such that a dissolved oxygen content of said composition is less than about 5 ppm.

11. The composition of claim 1, wherein said source of chlorine dioxide and said food grade acidulent are added to said water, such that a dissolved oxygen content of said composition is less than about 2 ppm.

12. The composition of claim 1, wherein a dissolved oxygen content of said composition is less than about 1 ppm.

13. A method for reducing odors emanating from animal discharges, comprising the steps of applying a dosage of said composition of claim 1 to food rations in an amount effective to reduce odors and feeding said food rations to an animal.

14. The method of claim 13, wherein said dosage is applied using application means delivering about 0.05 ounces per application ($0.14 \times 10^{-5}$ $m^3$ per application).

15. The method of claim 13, wherein said dosage is about one ounce per week ($2.96 \times 10^{-5}$ $m^3$ per week).

16. A process for manufacturing a composition for reducing odors emanating from animal discharges, said process consisting essentially of the steps of:

(a) providing water with a calcium carbonate content less than about 1000 ppm;

(b) adding chlorine dioxide to said water in an amount effective to reduce odors emanating from animal discharges; and (c) adding an acidulent to said water in sufficient quantity to adjust the pH of the composition to a value greater than about 7.

17. The process of claim 16, wherein said water has a calcium carbonate content less than about 500 ppm.

18. The process of claim 16, wherein said water has a calcium carbonate content less than about 300 ppm.

19. The process of claim 16, wherein said food grade acidulent is present in an amount sufficient to adjust the pH of the composition to a value greater than about 9.

20. The process of claim 16, wherein said food grade acidulent is present in an amount sufficient to adjust the pH of the composition to a value in a range of about 9.2 to 9.4.

21. The process of claim 16, wherein said source of chlorine dioxide and said food grade acidulent are added to said water, such that a dissolved oxygen content of said composition is less than about 5 ppm.

22. The process of claim 16, wherein said source of chlorine dioxide and said food grade acidulent are added to said water, such that a dissolved oxygen content of said composition is less than about 2 ppm.

23. The process of claim 16, wherein said source of chlorine dioxide and said food grade acidulent are added to said water, such that a dissolved oxygen content of said composition is less than about 1 ppm.

24. The process of claim 16, wherein said water is de-ionized water filtered by reverse osmosis.

25. The process of claim 16, wherein said water is distilled water.

26. The process of claim 16, wherein said food grade acidulent is selected from the group consisting of phosphoric acid, citric acid, malic acid, and acetic acid.

27. The process of claim 16, wherein said food grade acidulent is distilled vinegar.

28. A product for reducing odors emanating from animal discharges, comprising: a composition consisting essentially of:

(a) water with a calcium carbonate content less than about 1000 ppm;

(b) chlorine dioxide in an amount effective to reduce odors emanating from animal discharges; and (c) an acidulent in sufficient quantity to adjust the pH of the composition to greater than about 7;

disposed in a container which comprises a material that blocks the transmission of ultra-violet radiation.

29. The product of claim 28, wherein said water has a calcium carbonate content less than about 500 ppm.

30. The product of claim 28, wherein said water has a calcium carbonate content less than about 300 ppm.

31. The product of claim 28, wherein said food grade acidulent is present in an amount sufficient to adjust the pH of the composition to a value greater than about 9.

32. The product of claim 28, wherein said food grade acidulent is present in an amount sufficient to adjust the pH of the composition to a value in a range of about 9.2 to 9.4.

33. The product of claim 28, wherein said chlorine dioxide and said food grade acidulent are added to said water, such that a dissolved oxygen content of said composition is less than about 5 ppm.

34. The product of claim 28, wherein said chlorine dioxide and said food grade acidulent are added to said water, such that a dissolved oxygen content of said composition is less than about 2 ppm.

35. The product of claim 28, wherein said chlorine dioxide and said food grade acidulent are added to said water, such that a dissolved oxygen content of said composition is less than about 1 ppm.

36. The product of claim 28, further comprising application means for applying measured amounts of said composition to animal food rations.

37. The product of claim 36, wherein said application means is a spray applicator.

38. The product of claim 37, wherein said spray applicator applies a dosage of about 0.05 ounces per spray ($0.14 \times 10^{-5}$ $m^3$ per spray).

39. A method for reducing odors emanating from animal discharges, comprising the steps of applying a dosage of said composition of claim 1 to an animal in an amount effective to reduce odors emanating from animal discharges.

40. The method of claim 39, wherein said dosage is applied topically.

41. The method of claim 39, wherein said dosage is applied by swabbing said composition onto said animal.

42. The method of claim 39, wherein said dosage is applied to an animal's skin at an opening from which glandular excretions discharge.

43. The method of claim 39, wherein said dosage is applied in the genital region of an animal in heat.

44. A animal food product for reducing odors emanating from animal discharges, comprising said composition of claim 1 applied to animal food in an amount effective to reduce odors.

45. A product for reducing odors emanating from animal discharges, comprising a topical application including said composition of claim 1 in an amount effective to reduce odors.

46. The product of claim 45, wherein said topical application is an ointment.

47. The product of claim 45, wherein said topical application is a suppository.

* * * * *